United States Patent [19]

Hwang et al.

[11] Patent Number: 5,389,667
[45] Date of Patent: Feb. 14, 1995

[54] PYRAZOLE CONTAINING BENZOYL UREA DERIVATIVES, AND COMPOSITIONS

[75] Inventors: Ki J. Hwang; Kyung H. Park, both of Daejeon, Rep. of Korea

[73] Assignee: Korea Research Institute of Chemical Technology, Daejeon, Rep. of Korea

[21] Appl. No.: 39,373

[22] PCT Filed: Aug. 18, 1992

[86] PCT No.: PCT/KR92/00039

§ 371 Date: Jun. 18, 1993

§ 102(e) Date: Jun. 18, 1993

[87] PCT Pub. No.: WO93/04044

PCT Pub. Date: Mar. 4, 1993

[30] Foreign Application Priority Data

Aug. 20, 1991 [KR] Rep. of Korea .............. 91-14311

[51] Int. Cl.[6] ............... A01N 43/56; C07D 231/20; C07D 231/22
[52] U.S. Cl. ................... 514/407; 548/370.1
[58] Field of Search ............ 548/370.1; 514/407

[56] References Cited

U.S. PATENT DOCUMENTS 4,382,947 5/1983 Maurer et al. ............... 548/370.1

*Primary Examiner*—Robert W. Ramsuer
*Attorney, Agent, or Firm*—Kenyon & Kenyon

[57] ABSTRACT

The present invention is directed to benzoyl urea derivatives having pyrazole group which correspond to the following formula(I) and the insecticidal compositions containg the same are provided.

Said derivatives exhibit excellent insecticidal effects and bioactivities.

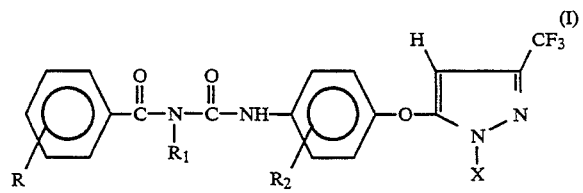

wherein,

R and $R_2$, as equivalent or different group respectively, are hydrogen, one or more halogen atoms selected from the group consisting of fluoride, chloride and bromide atom, lower alkoxy or nitro group;

$R_1$ is hydrogen atom or a lower alkyl group; and

X is a lower alkyl group or phenyl substituent.

2 Claims, No Drawings

PYRAZOLE CONTAINING BENZOYL UREA DERIVATIVES, AND COMPOSITIONS

BACKGROUND OF THE INVENTION

The present invention relates to novel benzoyl urea derivatives having a pryzole group which have active insecticidal properties as insect growth regulator. The present invention also relates to the insecticidal compositions comprising said derivatives and to the use of such compositions for killing and controlling insects.

Several kinds of benzoyl urea compounds have been developed as chitin inhibitor since Dimilin ® was introduced in the market. However most of them have not been commercialized due to the complicated manufacturing process and high cost although it has a better effect than Dimilin ®. For example, even though several benzoyl urea derivatives have been synthesized according to the disclosed Japanese Patent laid-open No. 85-193960 and 87-178561, European Patent No. 176868 and 52833, these manufacturing processes are too complicated to be improved.

Therefore, with consideration to the foregoing points the present inventors have developed new insecticidal compounds which exhibit broad spectrum and powerful insecticidal activities to various harmful insect.

Furthermore, they can be prepared via simple process starting from readily available raw chemicals compared with existing chitin inhibitor insecticide.

SUMMARY OF THE INVENTION

An object of the present invention is to provide a powerful benzoyl urea derivatives with a strong insecticidal activities toward various harmful insects and have a simple manufacturing process by using raw materials of low cost.

Another object is to provide the insecticidal compositions containing active compounds of said derivatives.

DETAILED DESCRIPTION OF THE INVENTION

The present invention is directed to benzoyl urea derivatives having pyrazole group which correspond to the following formula(I)

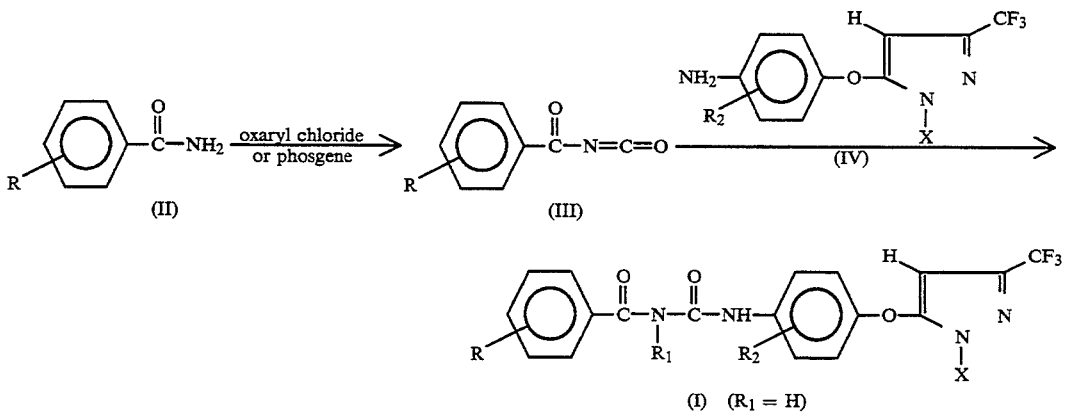

wherein,

R and R₂, as equivalent or different group respectively, are hydrogen, one or more halogen atoms selected from the group consisting of fluoride, chloride and bromide atom, lower alkoxy or nitro group;

R₁ is hydrogen atom or a lower alkyl group; and

X is a lower alkyl group or phenyl substituent.

In the present invention, the term "lower alkoxy group" and "lower alkyl group" designate a straight or branched chain alkoxy and alkyl group of 1 to 6 carbon atoms.

According to the present invention, firstly said benzoyl urea derivatives can be easily prepared by converting substituted benzamide derivatives of the following formula(II) to benzoyl isocyanate of the following formula(III) using oxaryl chloride or phosgene and reacting the compound of formula(III) with anilin derivatives of the following formula(IV) and an acid scavenger.

wherein, R, R₂ and X are defined as above; and R₁ is hydrogen atom.

In the above reaction, organic solvents such as benzene, toluene, xylene, chlorobenzene or 1,2-dichloroethane can be used for the reaction from substitutied benzamide derivatives of the formula(II) to benzoyl isocyanate of the formula(III), and then the completion of reaction is assumed when no more gas is produced. Toluene, xylene, chlorobenzene or 1,2-dichloroethane can be used as a solvent for obtaining the desired compound(I) by reacting isocyanate of the formula(III) with anilin derivatives of the formula(IV), and then 0.5~1 equivalent weight of tertiary amine, e.g. triethyl amine, is used as an acid scavenger.

If the acid scavenger is not added, the yield will be decreased due to coexisting hydrochloride which is produced during the formation of isocyanate(III). The completion of reaction for formation the desired compound(I) is when no more anilin derivative is remained. It can be easily checked by T.L.C. or G.C.

After completion of the reaction, the desired compound may be separated by well-known method as follows: the solid compound is obtained by recrystallization after filtered, and the remaining filtrate is washed with water to remove organic solvents, and then the desired compound can be obtained by recrystallization or purified by chromatography and identified by NMR, IR and MS.

Secondly, the desired compound(I) can be produced by reacting anilin derivatives of the formula(IV) with phosgene to obtain isocyanate of the following formula(V) and adding benzamide derivatives of the formula(II) and acid scavenger, as following reaction scheme.

or chlomatography, and it can be confirmed by NMR, IR and MS.

New benzoyl urea derivatives of said formula(I) according to the present invention are typically listed in Table 1.

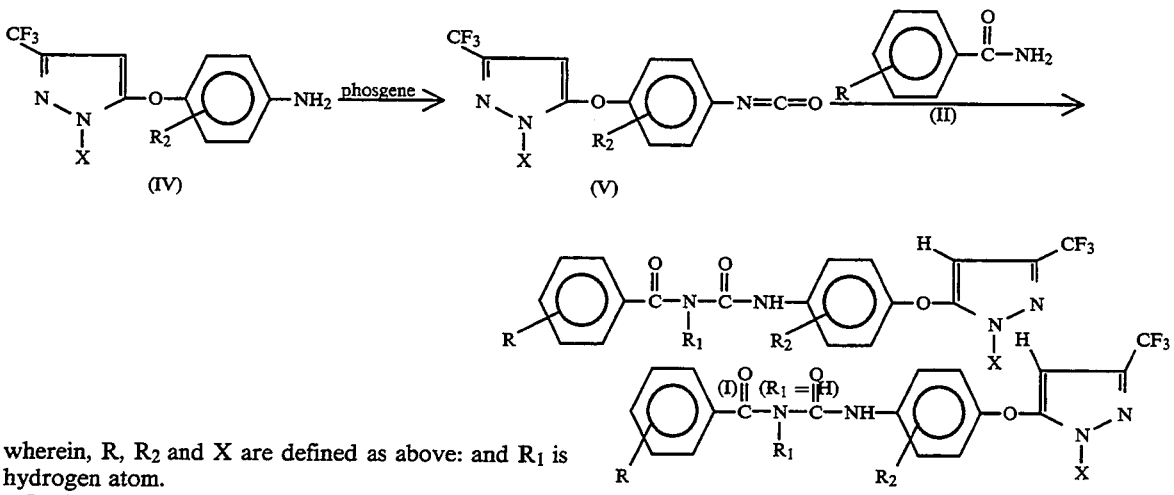

wherein, R, $R_2$ and X are defined as above: and $R_1$ is hydrogen atom.

In the above reaction, ethylacetate, tetrahydrofuran, benzene, toluene, chlorobenzene, xylene or 1,2-dichloroethane can be used as organic solvent for obtaining isocyanate compound(V) from anilin derivatives of the formula(IV). The completion of reaction is assumed when no more hydrogen chloride gas is produced.

Also, toluene, xylene or chlorobenzene can be used as organic solvent for the reaction of isocyanate derivatives(V) with benzamide derivatives(II), and then tertiary amine such as triethylamine can be used as an acid scavenger.

The completion of reaction is assumed when no more compound of formula(II) is remained. The identification of the completion, yield and the desired compound is same as the above first method.

According to the present invention, alkyl group can be introduced at $R_1$ position of the desired compound of formula(I) ($R_1$=H) by using alkylating reagent. For example, the compound(I), where $R_1$ is alkyl group, can be produced by treating methyliodide or ethyliodide with the compound of formula(I)($R_1$=H) and acid scavenger.

Acetonitrile, dimethylformamide or dimethylsulfoxide may be used as organic solvent and hydroxide of alkali metal or alkali earth metal, carbonate or tertiary amine may be used as acid combiner. The completion of reaction is assumed when no more compound of formula(I)($R_1$=H) remains, and it can be easily checked by T.L.C. or G.C. After completion of reaction for alkyl substitution, several processes can be applied for obtaining the desired compound from the reaction mixture. For example, after washing the reaction mixture with water to remove the used organic solvent, the desired compound can be obtained by recrystallization

TABLE 1

| Compound No. | R | $R_1$ | $R_2$ | X |
| --- | --- | --- | --- | --- |
| 1 | 2,6-$F_2$ | H | 2,5-$Cl_2$ | $CH_3$ |
| 2 | 2,6-$F_2$ | H | 2,5-$Cl_2$ | ⬡ |
| 3 | 2,6-$F_2$ | H | 2-OMe | $CH_3$ |
| 4 | 2,6-$F_2$ | H | 2-$CO_2$Me | $CH_3$ |
| 5 | 2,6-$F_2$ | H | 2,5-$F_2$ | ⬡ |
| 6 | 2,6-$F_2$ | H | 3-Cl | $CH_3$ |
| 7 | 2,6-$F_2$ | H | 3-Cl | ⬡ |
| 8 | 2,6-$F_2$ | H | 2,3,5,6-$F_4$ | $CH_3$ |
| 9 | 2,6-$F_2$ | H | 2,3,5,6-$F_4$ | ⬡ |
| 10 | 2-Cl | H | 2,3,5,6-$F_4$ | ⬡ |

TABLE 1-continued

| Compound No. | R | $R_1$ | $R_2$ | X |
|---|---|---|---|---|
| 11 | 2-F | H | 2,3,5,6-$F_4$ | phenyl |
| 12 | 2-Cl | H | 2,5-$Cl_2$ | phenyl |
| 13 | 2,6-$F_2$ | H | 3-$CF_3$ | phenyl |
| 14 | 2-Cl | H | 3-$CF_3$ | phenyl |
| 15 | 2-F | H | 3-$CF_3$ | phenyl |
| 16 | 2-Cl | H | 3-Cl | $CH_3$ |
| 17 | 2-F | H | 3-Cl | $CH_3$ |

The present invention is illustrated by following Examples, but should not be construed to be limited thereto.

EXAMPLE 1

Benzamide-2,6-difluoro-N-(((2.5-dichloro-4-(1-methyl-3-trifluoromethyl-5-pyrazoyl)oxyphenyl)amino)carbonyl) (Compound No. 1)

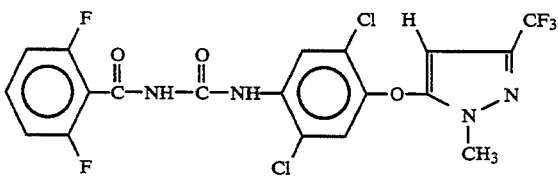

2,6-Difluorobenzamide(0.145 g, 0.92 mmole) and oxarylchloride(0.141 g, 1.11 mmole, 1.2 eq) were added to 1,2-dichloro ethane(6 ml) and the mixture was stirred at 100° C. for 20 hours. 2,5-Dichloro-4-o-(1-methyl-3-trifluormethyl-5-pyrazoyl)-anilin(0.3 g, 0.92 mmole) and triethyl amine(0.664 ml, 0.5 eq) were added and reacted at room temperature for one hour.

Organic solvent was removed under reduced pressure, and then ethyl acetate (60 ml) and water (40 ml) were added to the reaction mixture to collect ethyl acetate layer, which is dried with anhydrous magnesium sulfate. After removing ethyl acetate under reduced pressure, the desired product (0.311 g, yield 66%) was obtained as solid by chromatography(ethyl acetate:hexane=1:2).

m.p.: 213°~215° C.

$^1$H NMR($CDCl_3$+DMSO-$d_6$): δ 3.9(s. 3H), 5.8(s. 1H), 7.0~7.6(m. 4H), 8.6(s. 1H), 11.1(s. 1H), 11.3(s. 1H)

EXAMPLE 2

Benzamide-2,6-difluoro-N-(((2,5-dichloro-4-(1-phenyl-3-trifluoromethyl-5-pyrazoyl)oxyphenyl)amino)carbonyl) (Compound No. 5)

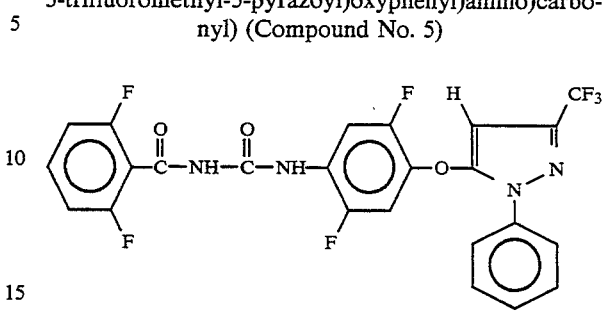

2,6-Difluorobenzamide(0.25 g, 1.59 mmole) and oxarylchloride(0.166 ml, 1.90 mmole, 1.2 eq) were added to 1,2-dichloroethane(6 ml), and the mixture was stirred at 100° C. for 20 hours. 2,5-Difluoro-4-o-(1-phenyl-3-trifluoromethyl-5-pyrazoyl)-anilin(0.564 g, 1.59 mmole) and triethylamine(0.11 ml, 0.5 eq) were added and reacted at room temperature for one hour.

Organic solvent was removed under reduced pressure, and then ethyl acetate (80 ml) and water (40 ml) were added to the reaction mixture to collect ethyl acetate layer, which is dried with anhydrous magnesium sulfate.

After removing ethyl acetate under reduced pressure, the desired product (0.45 g, yield: 52%) was obtained as solid by recrystallization (ethyl acetate+hexane). m.p.: 185°~187° C.

$^1$H NMR($CDCl_3$): δ 5.9(s. 1H), 7.0~8.2(m. 10H), 10.2(s. 1H), 11.0(s. 1H)

EXAMPLE 3

Benzamide-2,6-difluoro-N-(((3-chloro-4-(1-methyl-3-trifluoromethyl-5-pyrazoyl)oxyphenyl)amino)carbonyl) (Compound No. 6)

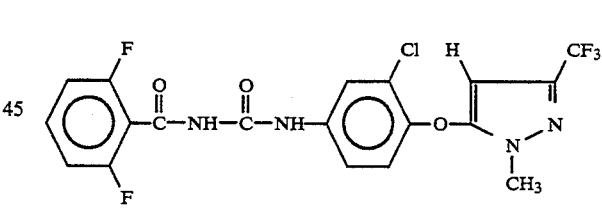

2,6-Difluoro benzamide(0.25 g, 1.59 mmole) and oxacrylchloride(0.166 ml, 1.90 mmole, 1.2 eq) were added to 1,2-dichloroethane (8 ml), and the mixture was stirred at 100° C. for 20 hours. 3-Chloro-4-o-(1-methyl-3-trifluoromethyl-5-pyrazoyl)-anilin(0.463 g, 1.59 mmole) and triethylamine(0.11 ml, 0.5 eq) were added and reacted at room temperature for one hour.

Organic solvent was removed under reduced pressure, and then ethyl acetate(80 ml) and water (40 ml) were added to the reaction mixture to collect ethyl acetate layer, which is dried with anhydrous magnesium sulfate.

After removing ethyl acetate under reduced pressure, the desired product(0.377 g, yield: 50%) was obtained as solid by recrystallization(ethyl acetate+hexane).

m.p.: 193°~195° C.

$^1$H NMR($CDCl_3$): δ 3.8(s. 3H), 5.8(s. 1H), 7.0~7.8(m. 6H), 10.1(s. 1H), 10.8(s. 1H)

EXAMPLE 4

Benzamide-2,6-difluoro-N-(((3-chloro-4-(1-phenyl-3-trifluoromethyl-5-pyrazoyl)oxyphenyl)amino)carbonyl) (Compound No. 7)

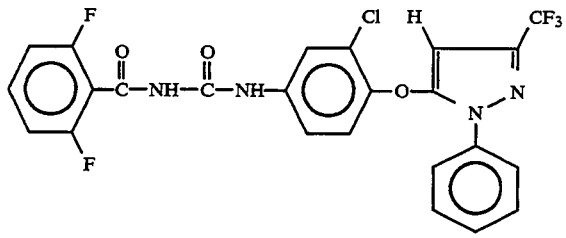

2,6-Difluorobenzamide(0.17 g, 1.131 mmole) and oxarylchloride(0.118 ml, 1.35 mmole, 1.2 eq) were added to 1,2-dichloroethane(6 ml), and the mixture was stirred at 100° C. 20 hours. 3-Chloro-4-o-(1-phenyl-3-tirfluoromethyl-5-pyrazoyl)-anilin(0.4 g, 1.131 mmole) and triethylamine(0.09 ml, 0.5 eq) were added and reacted at room temperature for one hour.

Organic solvent was removed under reduced pressure, and then ethyl acetate(70 ml) and water(40 ml) were added to the reaction mixture to collect ethyl acetate layer, which is dried with anhydrous magnesium sulfate. After removing ethyl acetate under reduced pressure, the desired product(0.31 g, yield: 51%) was obtained as solid by chromatography(ethyl acetate:hexane=1:5).

m.p.: 169°~172° C.

$^1$H NMR(CDCl$_3$): δ 5.9(s. 1H), 7.0~8.0(m. 1H), 9.8(s. 1H), 10.7(s. 1H)

EXAMPLE 5

Benzamide-2,6-difluoro-N-(((3-chloro-4-(1-phenyl-3-trifluoromethyl-5-pyrazoyl)oxyphenyl)amino)carbonyl) (Compound No. 8)

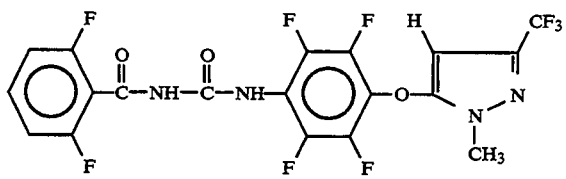

2,6-Difluorobenzamide(0.1 g, 0.636 mmole) and oxarylchloride(0.066 ml, 0.763 mmole, 1.2 eq) were added to 1,2-dichloroethane(6 ml), and the mixture was stirred at 100° C. for 20 hours. 2,3,5,6-Tetrafluoro-4-o-(1-methyl-3-trifluoromethyl-5-pyrazoyl)-anilin(0.209 g, 0.636 mmole) and triethylamine(0.044 ml, 0.5 eq) were added and reacted at room temperature for one hour.

Organic solvent was removed under reduced pressure, and then ethyl acetate(60 ml) and water(30 ml) were added to the reaction mixture to collect ethyl acetate layer, which is dried with anhydrous magnesium sulfate. After removing ethyl acetate under reduced pressure, the desired product(0.2 g, yield: 61%) was obtained as solid by chromatography(ethyl acetate:hexane=1:9).

m.p.: 215°~217° C.

$^1$H NMR(CDCl$_3$): δ 3.8(s. 3H), 5.8(s. 1H), 6.8~7.6(m. 3H), 9.1(s. 1H), 10.0(s. 1H)

EXAMPLE 6

Benzamide-2,6-difluoro-N-(((2,3,5,6-tetrafluoro-4-(1-phenyl-3-trifluoromethyl-5-pyrazoyl)oxyphenyl)amino)carbonyl) (Compound No. 9)

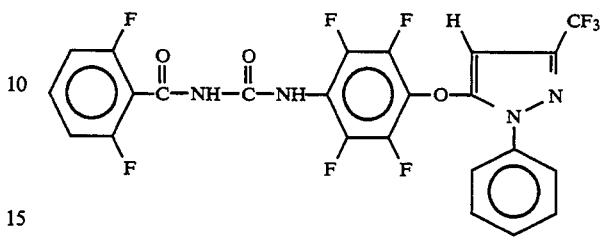

2,6-Difluorobenzamide(0.2 g, 1.27 mmole) and oxarylchloride(0.132 ml, 1.524 mmole, 1.2 eq) were added to 1,2-dichloroethane(8 ml), and the mixture was stirred at 100° C. for 20 hours. 2,3,5,6-Tetrafluoro-4-o-(1-phenyl-3-trifluoromethyl-5-pyrazoyl)-anilin(0.497 g, 1.27 mmole) and triethylamine(0.08 ml, 0.5 eq) were added at room temperature for one hour.

Organic solvent was removed under reduced pressure, and ethyl acetate(70 ml) and water(30 ml) were added to the reaction mixture to collect ethyl acetate layer, which is dried with anhydrous magnesium sulfate. After removing ethyl acetate under reduced pressure, the desired product(0.45 g, yield: 61%) was obtained as solid by chromatography(ethyl acetate:hexane=1:9).

m.p.: 198°~200° C.

$^1$H NMR(CDCl$_3$): δ 5.9(s. 1H), 6.9~7.8(m. 8H), 9.4(s. 1H), 10.2(s. 1H)

EXAMPLE 7

Benzamide-2-chloro-N-(((2,3,5,6-tetrafluoro-4-(1-phenyl-3-trifluoromethyl-5-pyrazoyl)oxyphenyl)amino)-carbonyl) (Compound No. 10)

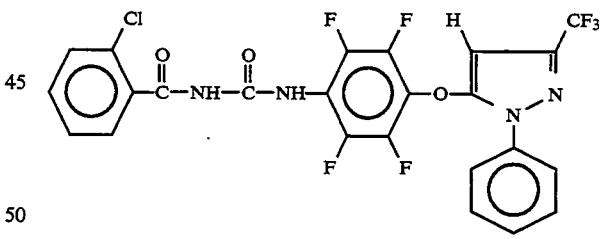

2-Chlorobenzamide(0.1 g, 0.64 mmole) and oxarylchloride(0.067 ml, 0.76 mmole, 1.2 eq) were added to 1,2-dichloroethane(7 ml), and the mixture was stirred at 100° C. for 20 hours. 2,3,5,6-tetrafluoro-4-o-(1-phenyl-3-trifluoromethyl-5-pyrazoyl)-anilin(0.25 g, 0.64 mmole) and triethyl amine(0.044 ml, 0.5 eq) were added and reacted at room temperature for one hour.

Organic solvent was removed under reduced pressure, and then ethyl acetate(70 ml) and water(30 ml) were added to the reaction mixture to collect ethyl acetate layer, which is dried with anhydrous magnesium sulfate. After removing ethyl acetate under reduced pressure, the desired product(0.21 g, yield: 57%) was obtained as solid by chromatography(ethyl acetate:hexane=1:9).

m.p.: 177°~179° C.

$^1$H NMR(CDCl$_3$): δ 5.9(s. 1H), 7.5~7.9(m. 9H), 9.4(s. 1H), 10.3(s. 1H)

EXAMPLE 8

Benzamide-2-fluoro-N-(((2,3,5,6-tetrafluoro-4-(1-phenyl-3-trifluoromethyl-5-pyrazoyl)oxyphenyl)amino)-carbonyl) (Compound No. 11)

2-Fluorbenzamide(0.088 g, 0.632 mmol and oxarylchloride(0.066 ml, 0.7 were added to 1,2-dichloroethane(7 ml), and the mixture was stirred at 100° C. for 20 hours. 2,3,5,6-Tetrafluoro-4-o-(1-phenyl-3-trifluoromethyl-5-pyrazoyl)-anilin(0.247 g, 0.632 mmole) and triethylamine(0.04 ml, 0.5 eq) were added and reacted at room temperature for one hour.

Organic solvent was removed under reduced pressure, and then ethyl acetate (60 ml) and water(30 ml) were added to the reaction mixture to collect ethyl acetate layer, which is dried with anhydrous magnesium sulfate. After removing ethyl acetate under reduced pressure, the desired product(0.197 g, yield: 56%) was obtained as solid by chromatography(ethyl acetate:hexane=1:9).

m.p.: 173°~175° C.

$^1$H NMR(CDCl$_3$): δ 6.0(s. 1H), 7.1~8.2(m. 9H), 9.2(d. 1H), 10.2(s. 1H)

EXAMPLE 9

Benzamide-2-chloro-N-(((3-chloro-4-(1-methyl-3-trifluoromethyl-5-pyrazoyl)oxyphenyl)amino)carbonyl) (Compound No. 16)

2-Chlorobenzamide(0.25 g, 1.60 mmole) and oxarylchloride(0.168 ml, 1.92 mmole, 1.2 eq) were added to 1,2-dichloroethane(7 ml), and the mixture was stirred at 100° C. for 20 hours. 3-Chloro-4-o-(1-methyl-3-trifluoromethyl-5-pyrazoyl)-anilin(0.468 g, 1.60 mmole) and triethylamine(0.11 ml, 0.5 eq) were added and reacted at room temperature for one hour.

Organic solvent was removed under reduced pressure, and then ethyl acetate(80 ml) and water(30 ml) were added to the reaction mixture to collect ethyl acetate layer, which is dried with anhydrous magnesium sulfate.

After removing ethyl acete under reduced process, the desired product(0.499 g, yield: 65%) was obtained as solid by chromatography(ethyl acetate:hexane=1:9).

m.p.: 201°~202° C.

$^1$H NMR(CDCl$_3$): δ 4.0(s. 3H), 5.8(s. 1H), 7.3~8.0(m. 7H), 9.9(s. 1H), 10.9(s. 1H)

EXAMPLE 10

Benzamide-2-fluoro-N-(((3-chloro-4-(1-methyl-3-trifluoromethyl-5-pyrazoyl)oxyphenyl)amino)carbonyl) (Compound No. 17)

2-Fluorobenzamide(0.143 g, 1.02 mmole) and oxarylchloride(0.107 ml, 1.23 mmole, 1.2 eq) were added to 1,2-dichloroethane(7 ml), and the mixture was stirred at 100° C. for 20 hours. 3-Chloro-4-o-(1-methyl-3-trifluoromethyl-5-pyrazoyl)-anilin(0.3 g, 1.02 mmole) and triethyl amine(0.071 ml, 0.5 eq) were added and reacted at room temperature for one hour.

Organic solvent was removed under reduced pressure, and then ethyl acetate(60 ml) and water(30 ml) were added to the reaction mixture to collect ethyl acetate layer, which is dried with anhydrous magnesium sulfate. After removing ethyl acetate under reduced pressure, the desired product(0.224 g, yield: 48%) was obtained as solid by chromatography(ethyl acetate:hexane=1:9).

m.p.: 179°~180° C.

$^1$H NMR(CDCl$_3$): δ 4.1(s. 3H), 5.9(s. 1H), 7.2~8.3(m. 7H), 9.1(d. 1H), 11.0(s. 1H)

EXAMPLE 11

Benzamide-2-chloro-N-(((3-chloro-4-(1-phenyl-3-trifluoromethyl-5-pyrazoyl)oxyphenyl)amino)carbonyl) (Compound No. 18)

2-Chlorobenzamide(0.132 g, 0.848 mmole) and oxarylchloride(0.088 ml, 1.90 mmole, 1.2 eq) were added to 1,2-dichloroethane(7 ml), and the mixture was stirred at 100° C. for 20 hours. 3-Chloro-4-o-(1-phenyl-3-trifluoromethyl-5-pyrazoyl)-anilin(0.3 g, 0.848 mmole) and triethylamine(0.059 ml, 0.5 eq) were added and reacted at room temperature for one hour.

Organic solvent was removed under reduced pressure, and then ethyl acetate(80 ml) and water(30 ml) were added to the reaction mixture to collect ethyl acetate layer, which is dried with anhydrous magnesium sulfate.

After removing ethyl acetate under reduced pressure, the desired product(0.2 g, yield: 44%) was obtained as solid by chromatography(ethyl acetate:hexane=1:9).

m.p.: 189°~190° C.

$^1$H NMR(CDCl$_3$): δ 5.9(s. 1H), 7.0~8.0(m. 12H), 9.7(s. 1H), 10.8(s. 1H)

EXAMPLE 12

Benzamide-2-chloro-N-(((2,5-difluoro-4-(1-methyl-3-trifluoromethyl-5-pyrazoyl)oxyphenyl)amino)carbonyl) (Compound No. 19)

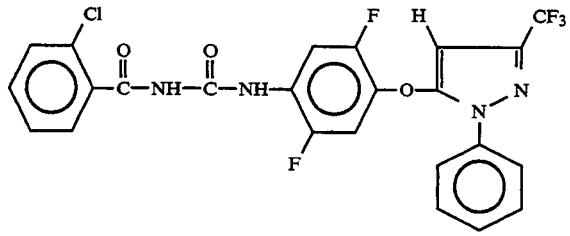

2-Chlorobenzamide(0.131 g, 0.844 mmole) and oxarylchloride(0.088 ml, 1.013 mmole, 1.2 eq) were added to 1,2-dichloroethane(7 ml), and the mixture was stirred at 100° C. for 20 hours. 2,5-Difluoro-4-o-(1-phenyl-3-trifluoro methyl-5-pyrazoyl)-anilin(0.3 g, 0.844 mmole) and triethylamine(0.058 ml, 0.5 eq) were added and reacted at room temperature for one hour.

Organic solvent was removed under reduced pressure, and then ethyl acetate(80 ml) and water(30 ml) were added to the reaction mixture to collect ethyl acetate layer, which is dried with anhydrous magnesium sulfate.

After removing ethyl acetate under reduced pressure, the desired product(0.2 g, yield: 43%) was obtained as solid by chromatography(ethyl acetate:hexane=1:9).

m.p.: 181°~182° C.

$^1$H NMR(CDCl$_3$): δ 5.9(s. 1H), 6.9~8.2(m. 11H), 10(s. 1H), 11.1(s. 1H)

EXAMPLE 13

Benzamide-2,6-difluoro-N-(((2,5-difluoro-4(1-methyl-3-trifluoromethyl-5-pyrazoyl)oxyphenyl)amino)carbonyl) (Compound No. 20)

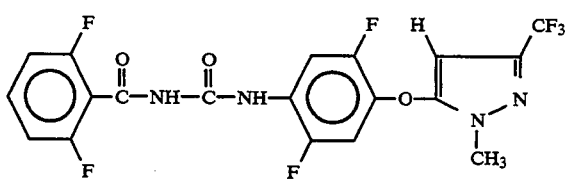

2,6-Difluorobenzamide(0.123 g, 0.784 mmole) and oxarylchloride(0.082 ml, 0.941 mmole, 1.2 eq) were added to 1,2-dichloroethane(7 ml), and the mixture was stirred at 100° C. for 20 hours. 2,5-Difluoro-4-o-(1-methyl-3-trifluoromethyl-5-pyrazoyl)-anilin(0.23 g, 0.784 mmole) and triethyl amine(0.054 ml, 0.5 eq) were added and reacted at room temperature for one hour.

Organic solvent was removed under reduced pressure, and then ethyl acetate(70 ml) and water(30 ml) were added to the reaction mixture to collect ethyl acetate layer, which is dried with anhydrous magnesium sulfate.

After removing ethyl acetate under reduced rpessure, the desired product(0.2 g, yield: 53%) was obtained as solid by crystallization(ethyl acetate+hexane).

m.p.: 203°~205° C.

$^1$H NMR(CDCl$_3$): δ 3.8(s. 3H), 5.8(s. 1H), 6.9~8.1(m. 5H), 10.1(s. 1H), 10.8(s. 1H)

EXAMPLE 14

Benzamide-2,6-difluoro-N-(((4-(1-methyl-3-trifluoromethyl-5-pyrazoyl)oxyphenyl)amino)carbonyl) (Compound No. 21)

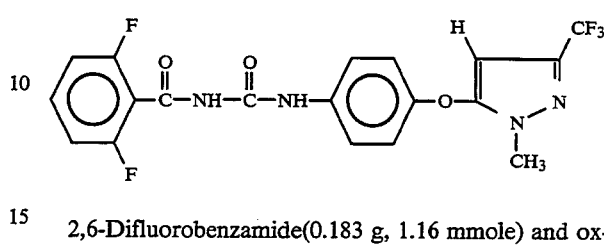

2,6-Difluorobenzamide(0.183 g, 1.16 mmole) and oxarylchloride(0.122 ml, 1.40 mmole, 1.2 eq) were added to 1,2-dichloroethane(7 ml), and the mixture was stirred at 100° C. for 20 hours. 4-o-(1-Methyl-3-trifluoromethyl-5-pyrazoyl)-anilin(0.3 g, 1.16 mmole) and triethylamine(0.08 ml, 0.5 eq) were added and reacted at room temperature for one hour.

Organic solvent was removed under reduced pressure, and then ethyl acetate(70 ml) and water(30 ml) were added to the reaction mixture to collect ethyl acetate layer, which is dried with anhydrous magnesium sulfate. After removing ethyl acetate under reduced pressure, the desired product (0.303 g, yield: 595) was obtained as solid by recrystallization(ethyl acetate+hexane).

m.p.: 203° C.

$^1$H NMR(CDCl$_3$): δ 3.8(s. 3H), 5.8(s. 1H), 6.8~7.5(m. 7H), 9.0(s. 1H), 10.4(s. 1H)

EXAMPLE 15

Benzamide-2,6-difluoro-N-(((3-trifluoromethyl-4-(1-methyl-3-trifluoromethyl-5-pyrazoyl)oxyphenyl)amino)carbonyl) (Compound No. 22)

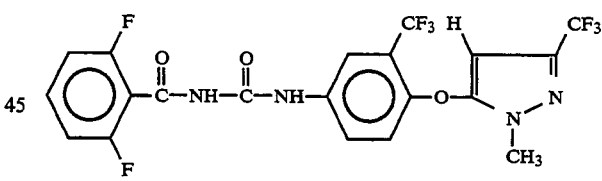

2,6-Difluorobenzamide(0.145 g, 0.922 mmole) and oxarylchloride(0.096 ml, 1.10 mmole, 1.2 eq) were added to 1,2-dichloroethane(6 ml), and the mixture was stirred at 100° C. for 20 hours. 3-Trifluoromethyl-4-o-(1-methyl-3-trifluoromethyl-5-pyrazoyl)-anilin(0.3 g, 0.922 mmole) and triethylamine(0.064 ml, 0.5 eq) were added and reacted at room temperature for one hour.

Organic solvent was removed under reduced pressure, and then ethyl acetate(70 ml) and water(30 ml) were added to the reaction mixture to collect ethyl acetate layer, which is dried with anhydrous magnesium sulfate.

After removing ethyl acetate under reduced pressure, the desired product(0.29 g, yield: 61%) was obtained as solid by chromatography(ethyl acetate:hexane=1:4).

m.p.: 203° C.

$^1$H NMR(CDCl$_3$): δ 3.8(s. 3H), 5.9(s. 1H), 6.9~7.9(m. 6H), 9.2(s. 1H), 10.7(s. 1H)

EXAMPLE 16

Benzamide-2,6-difluoro-N-(((3,5-dichloro-4-(1-methyl-3-trifluoromethyl-5-pyrazoyl)oxyphenyl)amino)carbonyl) (Compound No. 23)

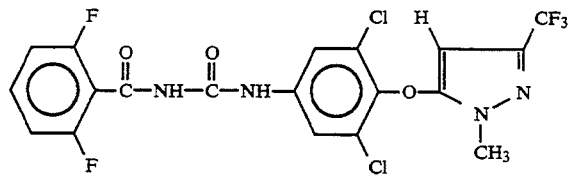

2,6-Difluorobenzamide(0.120 g, 0.766 mmole) and oxarylchloride(0.080 ml, 0.920 mmole, 1.2 eq) were added to 1,2-dichloro ethane(7 ml), and the mixture was stirred at 100° C. for 20 hours. 3,5-Dichloro-4-o-(1-methyl-3-trifluoromethyl-5-pyrazoyl)-anilin(0.25 g, 0.766 mmole) and triethylamine(0.053 ml, 0.5 eq) were added and reacted at room temperature for one hour.

Organic solvent was removed under reduced pressure, and then ethyl acetate(80 ml) and water(30 ml) were added to the reaction mixture to collect ethyl acetate layer, which is dried with anhydrous magnesium sulfate. After removing ethyl acetate under reduced pressure, the desired product(0.237 g, yield: 61%) was obtained as solid by chromatography(ethylacetate:hexane=1:5).

m.p.: 221° C.

$^1$H NMR(CDCl$_3$): δ 4.0(s. 3H), 5.6(s. 1H), 7.2~7.6(m. 5H), 10.8(s. 1H)

EXAMPLE 17

Benzamide-2,6-difluoro-N-(((3,5-dichloro-4-(1-phenyl-3-trifluoromethyl-5-pyrazoyl)oxyphenyl)amino)carbonyl) (Compound No. 24)

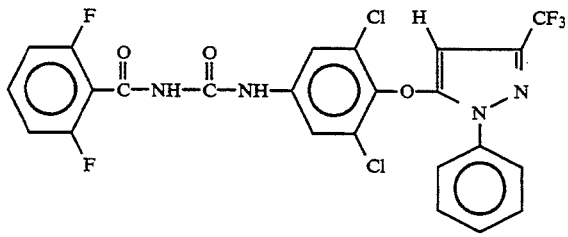

2,6-Difluorobenzamide(0.120 g, 0.766 mmole) and oxarylchloride(0.080 ml, 0.920 mmole, 1.2 eq) were added to 1,2-dichloroethane(7 ml), and the mixture was stirred at 100° C. for 20 hours. 3,5-Dichloro-4-o-(1-phenyl-3-trifluoromethyl-5-pyrazoyl)-anilin(0.297 g, 0.766 mmole) and triethylamine(0.053 ml, 0.5 eq) were added and reacted at room temperature for one hour.

Organic solvent was removed under reduced pressure, and then ethyl acetate(80 ml) and water(30 ml) were added to the reaction mixture to collect ethyl acetate layer, which is dried with anhydrous magnesium sulfate. After removing ethyl acetate under reduced pressure the desired product(0.274 g, yield: 62%) was obtained as solid by chromatography(ethylacetate:hexane=1:5).

m.p.: 236° C.

$^1$H NMR(CDCl$_3$): δ 5.6(s. 1H), 7.0~7.9(m. 10H), 10.2(s. 1H), 10.8(s. 1H)

EXAMPLE 18

Benzamide-2,6-difluoro-N-(((4-(1-phenyl-3-trifluoromethyl-5-pyrazoyl)oxyphenyl)amino)carbonyl) (Compound No. 25)

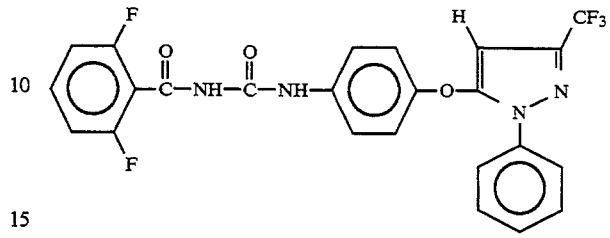

2,6-Difluorobenzamide(0.123 g, 0.783 mmole) and oxarylchloride(0.082 ml, 0.940 mmole, 1.2 eq) were added to 1,2-dichloroethane(7ml), and the mixture was stirred at 100° C. for 20 hours. 4-o-(1-Phenyl-3-trifluoromethyl-5-pyrazoyl)-anilin(0.25 g, 0.783 mmole) and triethylamine(0.054 ml, 0.5 eq) were added and reacted at room temperature for one hour.

Organic solvent was removed under reduced pressure, and then ethyl acetate(80 ml) and water(30 ml) were added to the reaction mixture to collect ethyl acetate layer, which is dried with anhydrous magnesium sulfate. After removing under reduced pressure, the desired product(0.25 g, yield=64%) was obtained as solid by chromatography(ethyl acetate:hexane=1:5).

m.p.: 215°~218° C.

$^1$H NMR(CDCl$_3$): δ 5.9(s. 1H), 6.9~7.9(m. 12H), 10.5(s. 1H), 10.8(s. 1H)

On the other hand, anilin derivatives of the formula(IV) as raw material used in the present invention may be synthesized by reacting the compound or its salt of formula(VI) with the compound of formula(VII), and then hydrogenolysis of the resulting compound of formula(VIII) as following reaction scheme.

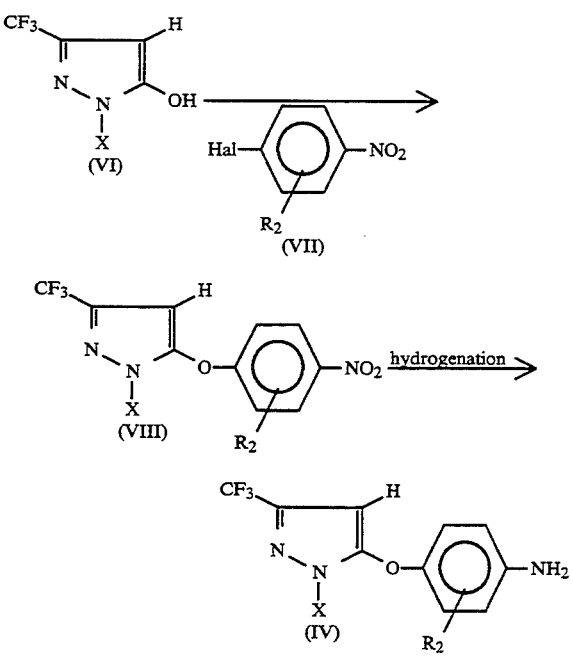

For the reaction of 5-hydroxy pyrazole compound of the formula(VI) with halogen substituted nitrobenzene of the formula(VII), common organic solvents such as dimethylformamide, dimethyl sulfoxide, acetonitrile or tetrahydrofuran can be used.

Alkali metal or alkali earth metal, carbonate, percarbonate or tertiary amine can be used as acid combiner. The completion of the reaction is assumed when no more two starting materials are remained, and it can be easily confirmed by T. L. C. or G. C.

After the completion of the reaction, the compound-(VIII) may be separated by well-known method as follows; for example, the solid compound is obtained by recrystallization after filtering, and remaining filtrate is washed with water to remove organic solvent, and then the compound(VIII) can be obtained by recrystallization or purfied by chromatography and identified by NMR, IR and MS.

Anilin derivatives of the formula(IV) can be produced by hydrogenolyzing said compound of the formula(VIII) under metal catalyst such as nikel or paradium with primary alcohol such as methanol or ethanol being used as organic solvent.

The reaction is assumed to be completed when no more substituted nitrobenzene compound of the formula(VIII) is remained. It can be confirmed by T.L.C. or G.C.

After the completion of hydrogenation, the compound(IV) can be seperated and purified as follows; the metal catalyst is removed by filtration, organic solvent is removed, and then the compound(IV) can be obtained by recrystallization or chromatography. They were identified by NMR, IR and MS.

The typical compounds of the formula(VIII) and (IV) as raw materials according to the present invention are respectively listed in Table 2 and 3.

TABLE 2

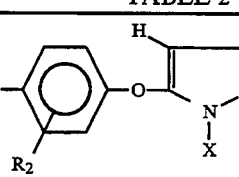

(VIII)

| Compound No. | X | $R_2$ |
|---|---|---|
| 29 | $CH_3$ | 2,5-$Cl_2$ |
| 30 | $CH_3$ | 2,5-$F_2$ |
| 31 | $CH_3$ | 3-Cl |
| 32 | $CH_3$ | 2,3,5,6-$F_4$ |
| 33 | $CH_3$ | 3-$CF_3$ |
| 34 | $CH_3$ | 2-Cl |
| 35 | $CH_3$ | H |
| 36 | $CH_3$ | 3,5-$Cl_2$ |
| 37 | $CH_3$ | 2-OMe |
| 38 | $CH_3$ | 2-$CO_2Me$ |
| 39 | Ph | 2,5-$Cl_2$ |
| 40 | Ph | 2,5-$F_2$ |
| 41 | Ph | 3-Cl |

TABLE 2-continued

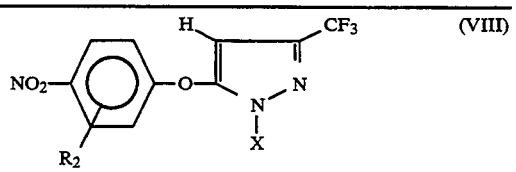

(VIII)

| Compound No. | X | $R_2$ |
|---|---|---|
| 42 | Ph | 2,3,5,6-$F_4$ |
| 43 | Ph | 3-$CF_3$ |
| 44 | Ph | 2-Cl |
| 45 | Ph | H |
| 46 | Ph | 3,5-$Cl_2$ |

TABLE 3

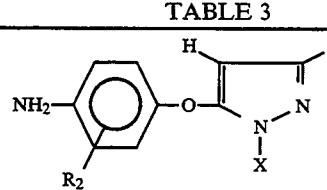

(IV)

| Compound No. | X | $R_2$ |
|---|---|---|
| 47 | $CH_3$ | 2,5-$Cl_2$ |
| 48 | $CH_3$ | 2,5-$F_2$ |
| 49 | $CH_3$ | 3-Cl |
| 50 | $CH_3$ | 2,3,5,6-$F_4$ |
| 51 | $CH_3$ | 3-$CF_3$ |
| 52 | $CH_3$ | 2-Cl |
| 53 | $CH_3$ | H |
| 54 | $CH_3$ | 3,5-$Cl_2$ |
| 55 | $CH_3$ | 2-OMe |
| 56 | $CH_3$ | 2-$CO_2Me$ |
| 57 | Ph | 2,5-$Cl_2$ |
| 58 | Ph | 2,5-$F_2$ |
| 59 | Ph | 3-Cl |

TABLE 3-continued

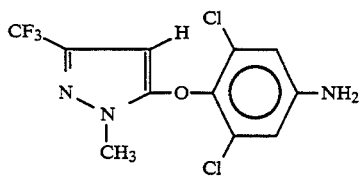

| Compound No. | X | R₂ |
|---|---|---|
| 60 | (phenyl) | 2,3,5,6-F₄ |
| 61 | (phenyl) | 3-CF₃ |
| 62 | (phenyl) | 2-Cl |
| 63 | (phenyl) | H |
| 64 | (phenyl) | 3,5-Cl₂ |

The following is a typical reaction condition for the preparation of the above new compounds shown in Table 2 and Table 3.

EXAMPLE 19

3,5-Dichloro-4-(1-methyl-3-trifluoromethyl-5-pyrazoyl)oxy-nitrobenzene (Compound No. 36)

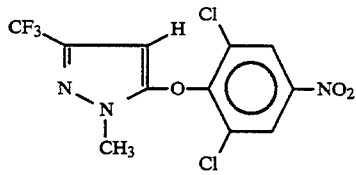

1-Methyl-3-trifluoromethyl-5-hydroxy pyrazole(1 g, 6.02 mmole), 3,4,5-trichloronitrobenzene(1.364 g, 602 mmole) and potassium carbonate(1.24 g, 9.03 mmole, 1.5 eq) were added in dimethylformamide(4 ml) and the mixture was stirred at 90°~100° C. for 30 minutes.

Ethyl acetate(80 ml) and water(30 ml) were added to the reaction mixture to collect ethyl acetate layer, which is to be dried with anhydrous magnesium. After removing ethyl acetate under reduced pressure, the desired product(1.5 g, yield: 70%) was obtained as solid by washing with hexane.

m.p.: 138°~140° C.

¹H NMR(CDCl₃): δ 3.9(s. 3H), 5.6(s. 1H), 8.3(s. 2H)

EXAMPLE 20

3,5-Dichloro-4-(1-methyl-3-trifluoromethyl-5-pyrazoyl)oxy-anilin(Compound No. 54)

3,5-Dichloro-4-o-(1-methyl-3-trifluoromethyl-5-pyrazoyl)-nitrobenzene (1.4 g, 3.93 mmole) and raney nickel (0.2 g) were added in methanol(30 ml) and reacted under hydrogen gas at 90° C. for 4 hours. The raney nickel was removed by filtration and methanol was removed under reduced pressure, and then the desired product(0.9 g, yield: 70%) was obtained as solid by chlormatography(ethyl acetate:hexane=1:9).

m.p.: 125° C.

¹H NMR(CDCl₃): δ 3.8(s. 2H), 3.9(s. 3H), 5.5(s. 1H), 6.6(s. 2H)

And also, the present invention is directed to the insecticidal compositions comprising the insecticidal compound of the present invention as an active compound. Said insecticidal compositions can be formulated in various forms, such as aqueous dispersions, emulsions, dusts, granules and so forth. These compositions are preferred to comprise one or more active compounds of the present invention with one or more suitable adjuvants such as carriers and diluents which are chemically inert to the active compound.

The exact concentration of the active compound in a composition thereof with an adjuvant therefor can vary; it is only necessary that the active compounds be present in sufficient amounts so as to make possible the application of an insecticidally effective dosage.

For example, in the case that the compositions are emulsions or aqueous dispersions, the amount of the active compound is preferred to range from 10 to 90% by weight.

And in the case of dust compositions, said amount is preferred to range from 0.1 to 30% by weight, also in the case of granule compositions, the amount is preferred to range from 1 to 30% by weight. But, the amount of the active compound in the compositions is somewhat variable according to the purpose of use of the compositions.

Preferred carriers to be employed in the compositions according to the present invention are liquid carriers which are selected from alcohols(i.e. monohydric alcohols like methanol, dihydric alcohols like ethyleneglycol, and trihydric alcohols like glycerine, etc.), ketones-(i.e. acetone, methylethylketone, etc.), ethers(i.e. dioxane, tetrahydrofuran, cellosolve, etc.), aliphatic hydrocarbons(i.e. gasoline, kerosene, etc.), hydrocarbon halides(i.e. chloroform, carbon tetrachloride, etc.), acid amides(i.e. dimethylformamide, etc.), esters(i.e. butyl acetate, ethyl acetate, glyceride, etc.), and nitriles (i.e. acetonitrile, etc.),and solid carriers which are selected from mineral particles such as kaoline, clay, bentonite, acid clay, talc, diatomaceous earth, silica and sand, and vegetable powers such as arbor. Said liquid carriers can be used separately or in company with one or more other liquid carriers.

The insecticidal composition of the present invention may include emulsifying agents, spreaders, dispersing agents or permeating agents. Also, the composition may include nonionic, anionic or cationic surfactants, for example, fatty acid soda or polyoxyalkylesters, alkylsulfonates or polyethyleneglycolethers.

On the other hand, one of the compounds of the present invention or compositions containing the same, can be advantageously employed in combination with one or more additional pesticidal compounds which are active agricultural chemicals. Such additional pesticidal compounds may be insecticides, herbicides, plant hormones and sterilizers, and if necessary, fertilizers.

| Composition 1 (Emulsion) | |
|---|---|
| | (by weight) |
| Compound No. 23 | 20% |
| xylene | 75% |
| polyoxyethylenglycolether | 5% |

The foregoing components were mixed to form an emulsion composition.

| Composition 2 (Dusts) | |
|---|---|
| | (by weight) |
| Compound No. 20 | 5% |
| kaoline | 94.6% |
| silicon (antifoaming agent) | 0.3% |
| polyoxyethylenglycolether | 0.1% |

The foregoing components were mixed to form a dust composition.

| Composition 3 (Aqueous dispersion) | |
|---|---|
| | (by weight) |
| Compound No. 24 | 30% |
| sodium lignosulfonate | 5% |
| polyoxyethyleneglycolether | 5% |
| bentonite | 60% |

The foregoing components were mixed to form an aqueous dispersion composition.

| Composition 4 (Granules) | |
|---|---|
| | (by weight) |
| Compound No. 19 | 10% |
| sodium lignosulfonate | 5% |
| bentonite | 85% |

The foregoing components were kneaded along with water and formed into a granule composition.

To demonstrate the superior effect of the compounds which were prepared in accordance with the present invention, test solutions with 500 ppm were prepared for the first insecticidal tests unless otherwise specifies.

The insecticidal rates(%) were calculated from these solutions. In the case of an insecticidal rate of 100%, the concentration of the test solution was gradually reduced until the $LC_{50}$ value, namely the concentration(ppm) which gives an insecticidal rate of 50%, was determined.

This test is illustrated by the following examples, but should not be construed to be limited thereto.

TEST 1

Insecticidal test for Diamond-backmoth

Diamond-backmoths(Plutella Xylostella Linnaeus) were successively reared using cabbages, and third instar larvae thereof were tested. For the insecticidal test, a piece of cabbage leaf 9 cm in diameter was dipped in a test solution for 30 minutes and air-dried for 30 minutes. The dried piece of cabbage leaf was put in a petri dish, and 10 of the third instar larvae were inoculated therein. The petri dish was capped and placed in a incubator. Till 120 hours after 24 hours, the number of killed moths was examined to determine the insecticidal rate(%), and then the tested cabbage leaf was replaced to new one every 48 hours.

The results are shown in Table 4.

TABLE 4

| Compound No. | Insecticidal Rate(%) | Compound No. | Insecticidal Rate(%) |
|---|---|---|---|
| 2 | 100 | 16 | 100 |
| 5 | 100 | 17 | 100 |
| 6 | 100 | 18 | 100 |
| 7 | 100 | 19 | 100 |
| 8 | 40 | 20 | 70 |
| 9 | 80 | 22 | 100 |
| 10 | 80 | 23 | 100 |
| 12 | 100 | 24 | 100 |
| 13 | 100 | 26 | 100 |
| 14 | 100 | no treatment | 0 |
| 15 | 100 | | |

Those compounds which produced an insecticidal rate of 100% at 500 ppm and, for comparison, commercial insecticidals(controls) were tested according to the method mentioned above, and the $LC_{50}$ values were determined.

The results are shown in Table 5.

TABLE 5

| Compound No. | $LC_{50}$ (ppm) | Compound No. | $LC_{50}$ (ppm) |
|---|---|---|---|
| Dimilin(control) | 100~125 | 16 | 50 |
| Chlorofluazuron(control) | 0.035 | 17 | 10 |
| 2 | 20 | 18 | 5 |
| 5 | 2.5 | 19 | 3 |
| 6 | 20 | 22 | 0.9 |
| 7 | 40 | 23 | 0.15 |
| 13 | 3 | 24 | 0.5 |
| 14 | 10 | | |

TEST 2

Insecticidal test for Tobacco cutworm

Tobacco cutworms(Spodop-tera litura) were successively reared using cabbages, and third instar larvae thereof were tested. For the insecticidal test, a piece of cabbage leaf 9 cm in diameter was dipped in a test solution for 30 seconds and air-dried for 30 minutes. The dried piece of cabbage leaf was put in a petri dish 9 cm in diameter, and 10 of the third instar larvae were inoculated therein. The petri dish was placed in an incubator, and till 120 hours after 24 hours, the number of killed cutworms was examined to determine the insecticidal rate(%). The tested cabbage leaf was replaced to new one every 48 hours.

The results are shown in Table 6.

TABLE 6

| Compound No. | Insecticidal Rate(%) | Compound No. | Insecticidal Rate(%) |
|---|---|---|---|
| 2 | 100 | 16 | 100 |
| 5 | 100 | 17 | 100 |
| 6 | 100 | 18 | 100 |
| 7 | 100 | 19 | 100 |
| 8 | 100 | 20 | 100 |
| 9 | 80 | 21 | 100 |
| 10 | 80 | 22 | 100 |
| 11 | 60 | 23 | 100 |
| 12 | 100 | 24 | 100 |
| 13 | 100 | 26 | 100 |
| 14 | 100 | no treatment | 0 |
| 15 | 100 | | |

Those compounds which produced an insecticidal rate of 100% at 500 ppm and for comparison, commercial insecticidals(controls) were tested according to the method mentioned above, and the $LC_{50}$ values were determined.

The results are shown in Table 7.

TABLE 7

| Compound No. | $LC_{50}$ (ppm) | Compound No. | $LC_{50}$ (ppm) |
|---|---|---|---|
| Dimilin(control) | 3.3 | 17 | 1.5 |
| Chlorofluazuron(control) | 0.022 | 18 | 3 |
| 2 | 0.7 | 19 | 0.7 |
| 5 | 0.04 | 20 | 0.2 |
| 6 | 0.04 | 21 | 0.4 |
| 7 | 0.15 | 22 | 0.4 |
| 8 | 3.5 | 23 | 0.2 |
| 13 | 7 | 24 | 0.06 |
| 14 | 1.5 | 26 | 4 |
| 16 | 5 | | |

From the results of said tests, it is demonstrated that the benzoyl urea derivatives having pyrazole group according to the present invention exhibit excellent bioactivity against Diamond-backmoth and Tobacco cutworm; namely similar activity as chlorfluazuron but for superior to Dimilin.

And also, the present noble benzoyl urea derivatives can be prepared cheaply via simple process starting form readily available raw material compared with existing high priced chitin inhibitor insecticides.

What is claimed is;

1. A compound of benzoyl urea derivatives having pyrazole group which correspond to the following formula(I).

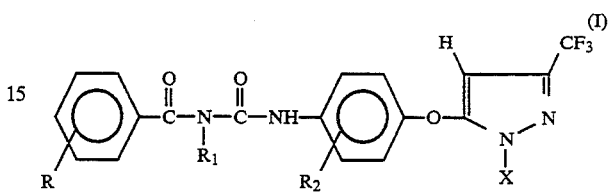

wherein,

R and $R_2$, as equivalent or different group respectively, are hydrogen, one or more halogen atoms selected from the group consisting of fluoride, chloride and bromide atom, lower alkoxy or nitro group;

$R_1$ is hydrogen atom or a lower alkyl group; and

X is a lower alkyl group or phenyl substituent.

2. An insecticidal composition containing active compound corresponding to the formula(I).

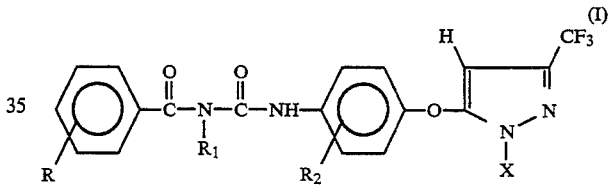

wherein, R, $R_1$, $R_2$ and X are defined as the above claim 1.

* * * * *